United States Patent [19]

Gould et al.

[11] Patent Number: 5,693,758

[45] Date of Patent: Dec. 2, 1997

[54] IMMUNOGLOBULIN E COMPETITOR

[75] Inventors: Hannah Jane Gould, London; Birgit Anna Helm, Loughton; Philip John Henry Benedict Marsh, London, all of England

[73] Assignee: 501 Research Corporation Limited, London, United Kingdom

[21] Appl. No.: 454,605

[22] Filed: May 31, 1995

Related U.S. Application Data

[63] Continuation of Ser. No. 993,970, Dec. 17, 1992, abandoned, which is a continuation of Ser. No. 392,528, filed as PCT/GB88/01018, Nov. 18, 1988 published as WO89/04834, Jun. 1, 1989, abandoned.

[30] Foreign Application Priority Data

Nov. 19, 1987 [GB] United Kingdom ............ 8727045

[51] Int. Cl.⁶ .................................................. C07K 14/47
[52] U.S. Cl. .................................................. 530/350
[58] Field of Search ...................................... 530/350

[56] References Cited

FOREIGN PATENT DOCUMENTS

| 0269455 | 1/1988 | European Pat. Off. . |
| 0257114 | 2/1988 | European Pat. Off. . |

OTHER PUBLICATIONS

Coleman et al. European J. immunol. 1985 15: 966–969.
Geha et al. Nature vol. 315 13 Jun. 1985 p. 577.
William Paul *Fundamental Immunology* Raven Press Mar. 1985.
Vercelli et al. Abstract Clinical Research Apr. 1987.
Lasky et al. Cell vol. 50 975–985 1987.
Dorrington, Keith J. and Benich, Hans H., "Structure–Function Relationships in Human Immunoglobulin E", Immunological Rev. 41:3–25 (1978).

*Primary Examiner*—Lila Feisee
*Assistant Examiner*—Nancy A. Johnson
*Attorney, Agent, or Firm*—Nixon & Vanderhye P.C.

[57] ABSTRACT

A polypeptide competitor or analogue for human Immunoglobulin E (IgE) low affinity sites comprises a polypeptide which has a sequence of amino acid which has a sequence of amino acids which is shown in Table I. This amino acid sequence corresponds to amino acids 340 to 439 of the epsilon heavy chain of IgE. A particularly preferred polypeptide competitor has a sequence of amino acids corresponding to amino acids 340 to 547 of the epsilon heavy chain of IgE as set out in Table V herein, which also shows the corresponding DNA sequence coding therefor. Such a polypeptide may also include additional short sequences at the beginning and/or end of the core sequence which are physiologically harmless and do not contribute to the ability of the core sequence to compete with native IgE for the low affinity receptor sites on human cells. The polypeptide may be produced synthetically or by expression from *Escherichia coli* containing a plasmid having a DNA segment coding for the polypeptide.

3 Claims, 3 Drawing Sheets

IMMUNOGLOBULIN E COMPETITOR

This is a continuation of application Ser. No. 07/993,970, filed Dec. 17, 1992, now abandoned, which is a continuation of 07/392,528, filed as PCT/GB88/01018, Nov. 18, 1988 published as WO89/04834, Jun. 1, 1989, now abandoned.

This invention relates to a competitor or analogue for human Immunoglobulin E (IgE). More particularly, the invention is concerned with a polypeptide which competes with IgE for low-affinity receptor sites.

Our co-pending International Patent Application No. PCT/GB87/00466 (International Patent Publication No. WO88/00204 published Jan. 14, 1988) describes and claims a polypeptide competitor for IgE which has a monomeric chain of seventy-six amino acids from the second and third domains of the human IgE sequence, corresponding to amino acid residues 301 to 376 of the full IgE heavy chain sequence reported by Bennich (Progress in Immunology II, Vol.I, July 1974, pp 49–58 and Int. Arch. Allergy App. Immunol. 53, 459). This polypeptide binds to high-affinity Fc receptors for IgE (FcER$_1$) which exist particularly on mast cells and basophils, thereby inhibiting the biological responses, such as exocytosis or degranulation, which take place when antigen specific IgE binds to and crosslinks such receptor sites in the presence of antigen.

In the human immune system, the principal role of IgE is believed to be to provide immunity to parasites. It also, however, mediates Type I hypersensitivity which is an allergic response leading to the manifestation of such symptoms as hay fever and asthma. Briefly, the mechanism of the allergic response is that on encountering a normally innocuous antigen such as pollen, synthesis of antigen-specific IgE by B-cells is initiated. The antigen-specific IgE then binds to mast cell receptor sites via its Fc region and thereafter any further encounter with the antigen triggers degranulation of the mast cells releasing mediators, principally histamine, resulting in the acute inflammatory symptoms typical of Type I hypersensitivity.

Structurally, IgE, in common with the other immunoglobulins, comprises two heavy and two light chains, the epsilon heavy chain having five domains, a variable domain VH and constant domains CH1 to CH4. The molecular weight of IgE is in the region of 188,000 of which the heavy chain accounts for about 72,500, representing a sequence of approximately 550 amino acid residues.

It has been reported (Nature, vol.315, 1985, No.6020, pp 577-578) that a peptide sequence of 330 amino-acids corresponding to amino acid residues 218 to 547 (in accordance with the numbering given by Bennich, Progress in Immunology II, vol I, July 1974, pp 49–58, as modified in a subsequent paper by Dorrington, K. J. and Bennich, H. in Immunol. Rev. (1978) 41:3 at page 7) of the epsilon heavy chain of IgE has an inhibitory effect on the release of mediators from human mast cells. The 330 amino-acid sequence exists as a dimer consisting of two chains of amino-acids, each of 330 amino-acids in length, linked by disulphide bonds.

U.S. Pat. Nos. 4,171,299 and 4,161,522 disclose that an oligopeptide containing from three to ten amino acids in a sequence selected from a portion of amino acids 265 to 537 of the Bennich nomenclature (see reference above) of the Fc region of human IgE will block Fc receptors of mast cells thus inhibiting degranulation and release of mediators such as histamine. The most active of these oligopeptides is identified as the pentapeptide Asp-Ser-Asp-Pro-Arg (called HEPP: Human Immunoglobulin E Polypeptide) derived from the amino acid sequence 330 to334 of the IgE heavy chain. In native IgE amino acid 332 is asparagine, but it is suggested-in these Patents that substitution of asparagine by aspartic acid leads to substantial enhancement of the blocking activity.

In the Patents mentioned above the full sequence which is attributed to Bennich (Progress in Immunology II, Vol I, July 1974, pp 49–58) is quoted and shows aspartic acid at location 332. However, Bennich himself later asserts (Int. Arch. Allergy Appl. Immunol. 53, 459 ) that asparagine resides at that location. Bennich also reports that neither of the peptides Asp-Ser-Asp-Pro-Arg nor Asp-Ser-Asn-Pro-Arg has any blocking activity. Determination of the gene sequence has shown that amino acid 332 is asparagine and not aspartic acid. In European Patent Publication No. 0102634 asparagine and not aspartic acid is correctly quoted at the equivalent location.

Further, it is also reported that the specific activity of HEPP is low requiring excessively large doses for any significant physiological effect.

It is known that IgE epsilon chain fragments may be synthesised in *Escherichia coli* by cloning and expression of the DNA sequences coding for the appropriate domains of the IgE chain (Eur. J. Immunol. 1985, 15:966–969 and Proc. Natl. Acad. Sc. USA, vol.81, 1984, 2955–2959).

Native IgE binds also to low-affinity receptors (FcER$_2$) on cells such as lymphocytes, eosinophils, monocytes and platelets to activate the effector functions of these cells, for example, IgE-dependent parasite-killing by eosinophils. FcER$_2$ receptors on B lymphocytes has also been implicated in the transduction of growth signals and in B cell activation. FcER$_1$ and FcER$_2$ are structurally unrelated proteins and can be expected to recognise different sites on the Fc region of IgE.

An object of the present invention is to provide a polypeptide which binds to the type 2 low-affinity Fc receptors (FcER$_2$ ).

According to the present invention there is provided a competitor for Immunoglobulin E low affinity receptor sites comprising a polypeptide having the sequence of amino acid residues 340 to 439 of the Bennich enumeration, shown in Table I below.

TABLE I

| | |
|---|---|
| 340 | A—Leu—Ser—Arg—Pro—Ser—Pro—Phe—Asp—Leu— |
| 349 | Phe—Ile—Arg—Lys—Ser—Pro—Thr—Ile—Thr—Cys— |
| 359 | Leu—Val—Val—Asp—Leu—Ala—Pro—Ser—Lys—Gly— |
| 369 | Thr—Val—Asn—Leu—Thr—Trp—Ser—Arg—Ala—Ser— |
| 379 | Gly—Lys—Pro—Val—Asn—His—Ser—Thr—Arg—Lys— |
| 389 | Glu—Glu—Lys—Gln—Arg—Asn—Gly—Thr—Leu—Thr— |
| 399 | Val—Thr—Ser—Thr—Leu—Pro—Val—Gly—Thr—Arg— |
| 409 | Asp—Trp—Ile—Glu—Gly—Glu—Thr—Tyr—Gln—Cys— |
| 419 | Arg—Val—Thr—His—Pro—His—Leu—Pro—Arg—Ala— |
| 429 | Leu—Met—Arg—Ser—Thr—Thr—Lys—Thr—Ser—Gly— |
| 439 | Pro—B. |

The group A in Table I is a hydrogen atom or an amino acid sequence which may include a chain initiating amino acid sequence and which includes at most a part only of the natural sequence of amino acid residues of the heavy chain of Immunoglobulin E, said part of said natural sequence forming all or a part of the sequence of amino acid residues 301 to 339 of the Bennich enumeration and B is a hydrogen atom or an amino acid sequence capable of forming a dimer with a like amino acid sequence B.

A may be an amino acid sequence which corresponds to a part of the natural amino acid sequence of the heavy chain of Immunoglobulin E extending from residue 339 at the C-terminal end of the group A back up to and including residue 291 using the Bennich enumeration. It may include only a part of this 301 to 339 sequence. A may be or include an inert polypeptide sequence, preferably an inert oligopeptide sequence, that does not interfere with the ability of the polypeptide to compete for the Immunoglobulin E low affinity receptor sites.

B may be any amino acid sequence that can form a dimer structure with a like group B and that does not interfere with the ability of the polypeptide competitor to compete for the Immunoglobulin E low affinity receptor sites. It may correspond to a part of the IgE heavy chain sequence commencing at residue 440 extending as far as, for example, residue 547, using the Bennich enumeration. Alternatively it can be a fragment of another protein, e.g. a mouse gamma-2b chain. It will usually be preferred that, when A represents or includes a chain initiating amino acid sequence, such a sequence contains no more than about 20 amino acid residues, and normally no more than about 10 such residues, e.g. 4 or 5.

In one preferred form of polypeptide competitor according to the invention A represents a hydrogen atom or a chain initiating amino acid sequence, X, such as Met-Asp-Pro-Arg- (the corresponding nucleotide sequence for which is ATG GAT CCG CGC) and B represents the sequence of amino acid residues 440 to 547 of the Bennich enumeration set out in Table II below.

TABLE II

| | |
|---|---|
| 440 | —Arg—Ala—Ala—Pro—Glu—Val—Tyr—Ala—Phe—<br>CGT GCT GCC CCG GAA GTC TAT GCG TTT |
| 449 | Ala—Thr—Pro—Glu—Trp—Pro—Gly—Ser—Arg—Asp—<br>GCG ACG CCG GAG TGG CCG GGG AGC CGG GAC |
| 459 | Lys—Arg—Thr—Leu—Ala—Cys—Leu—Ile—Gln—Asn—<br>AAG CGC ACC CTC GCC TGC CTG ATC CAG AAC |
| 469 | Phe—Met—Pro—Glu—Asp—Ile—Ser—Val—Gln—Trp—<br>TTC ATG CCT GAG GAC ATC TCG GTC CAG TGG |
| 479 | Leu—His—Asn—Glu—Val—Gln—Leu—Pro—Asp—Ala—<br>CTG CAC AAC GAG GTG CAG CTC CCC GAC GCC |
| 489 | Arg—His—Ser—Thr—Thr—Gln—Pro—Arg—Lys—Thr—<br>CGC CAC AGC ACG ACG CAG CCC CGC AAG ACC |
| 499 | Lys—Gln—Ser—Gly—Phe—Phe—Val—Phe—Ser—Arg—<br>AAG GCC TCC GGC TTC TTC GTC TTC AGC CGC |
| 509 | Leu—Gln—Val—Thr—Arg—Ala—Glu—Trp—Glu—Gln—<br>CTG GAG GTC ACC AGG GCC GAA TGG GAG CAG |
| 519 | Lys—Asp—Glu—Phe—Ile—Cys—Arg—Ala—Val—His—<br>AAA GAT GAG TTC ATC TGC CGT GCA GTG CAT |
| 529 | Glu—Ala—Ala—Ser—Pro—Ser—Gln—Thr—Val—Gln—<br>GAG GCA GCG AGC CCC TCA CAG ACC GTC CAG |
| 539 | Arg—Ala—Val—Ser—Val—Asn—Pro—Gly—Lys—[Stop]<br>CGA GCG GTG TCT GTA AAT CCC GGT AAA TGA. |

The invention further encompasses a polypeptide competitor as set out in Table I herein wherein A represents the sequence of amino acid residues 301 to 339 of the Bennich enumeration set out in table III below.

TABLE III

| | |
|---|---|
| 301 | Gln—Lys—His—Trp—Leu—Ser—Asp—Arg—Thr—Tyr— |
| 311 | Thr—Cys—Gln—Val—Thr—Tyr—Gln—Gly—His—Thr— |
| 321 | Phe—Glu—Asp—Ser—Thr—Lys—Lys—Cys—Ala—Asp— |
| 331 | Ser—Asn—Pro—Arg—Gly—Val—Ser—Ala—Tyr—. |

A particularly preferred polypeptide of this type has a residue B which represents the sequence of amino acids to be formed in a mouse gamma-2b chain whose structure and nucleotide sequence are set out in Table IV below.

TABLE IV

Pro—Gln—Val—Tyr—Ile—Leu—Pro—Pro—Pro—Ala—
CCA CAA GTA TAC ATC TTG CCG CCA CCA GCA
Glu—Gln—Leu—Ser—Arg—Lys—Asp—Val—Ser—Leu—
GAG CAG TTG TCC AGG AAA GAT GTC AGT CTC
Thr—Cys—Leu—Val—Val—Gly—Phe—Asn—Pro—Gly—
ACT TGC CTG GTC GTG GGC TTC AAC CCT GGA
Asp—Ile—Ser—Val—Glu—Trp—Thr—Ser—Asn—Gly—
GAC ATC AGT GTG GAG TGG ACC AGC AAT GGG
His—Thr—Glu—Glu—Asn—Tyr—Lys—Asp—Thr—Ala—
CAT ACA GAG GAG AAC TAC AAG GAC ACC GCA
Pro—Val—Leu—Asp—Ser—Asp—Gly—Ser—Tyr—Phe—
CCA GTC CTA GAC TCT GAC GGT TCT TAC TTC
Ile—Tyr—Ser—Lys—Leu—Asp—Ile—Lys—Thr—Ser—
ATA TAC AGC AAG CTC GAT ATA AAA ACA AGC
Lys—Trp—Glu—Lys—Thr—Asp—Ser—Phe—Ser—Cys—
AAG TGG GAG AAA ACA GAT TCC TTC TCA TGC
Asn—Val—Arg—His—Glu—Gly—Leu—Lys—Asn—Tyr—
AAC GTG AGA CAC GAG GGT CTG AAA AAT TAC
Tyr—Leu—Lys—Lys—Thr—Ile—Ser—Arg—Ser—Pro—
TAC CTG AAG AAG ACC ATC TCC CGG TCT CCG
Gly—Lys [Stop]
GGT AAA TGA.

The invention provides in particular a competitor for Immunoglobulin E low affinity receptor sites comprising a polypeptide having the sequence of amino acid residues 340 to 547 of the Bennich enumeration, shown in Table V below.

Further the invention provides a DNA having the nucleotide sequence also shown in Table V below.

TABLE V

| | |
|---|---|
| 340 | X—Leu—Ser—Arg—Pro—Ser—Pro—Phe—Asp—Leu—<br>CTA AGC CGG CCC AGC CCG TTC GAC CTG |
| 349 | Phe—Ile—Arg—Lys—Ser—Pro—Thr—Ile—Thr—Cys—<br>TTC ATC CGC AAG TCG CCC ACG ATC ACC TGT |
| 359 | Leu—Val—Val—Asp—Leu—Ala—Pro—Ser—Lys—Gly—<br>CTG GTC GTC GAC CTG GCA CCC AGC AAG GGG |
| 369 | Thr—Val—Asn—Leu—Thr—Trp—Ser—Arg—Ala—Ser—<br>ACC GTG AAC CTG ACC TGG TCC CGC GCC AGT |
| 379 | Gly—Lys—Pro—Val—Asn—His—Ser—Thr—Arg—Lys—<br>GCG AAG CTT GTG AAC CAC TCC ACC AGA AAG |
| 389 | Glu—Glu—Lys—Gln—Arg—Asn—Gly—Thr—Leu—Thr—<br>GAG GAG AAG CAG CGC AAT GGC ACG TTA ACC |
| 399 | Val—Thr—Ser—Thr—Leu—Pro—Val—Gly—Thr—Arg—<br>GTC ACG TCC ACC CTG CCG GTG GGC ACC CGA |
| 409 | Asp—Trp—Ile—Glu—Gly—Glu—Thr—Tyr—Gln—Cys—<br>GAC TGG ATC GAG GGG GAC ACC TAC CAG TGC |
| 419 | Arg—Val—Thr—His—Pro—His—Leu—Pro—Arg—Ala—<br>AGG GTG ACC CAC CCC CAC CTG CCC AGG GCC |
| 429 | Leu—Met—Arg—Ser—Thr—Thr—Lys—Thr—Ser—Gly—<br>CTC ATG CGG TCC ACG ACC AAG ACC AGC GCC |
| 439 | Pro—Arg—Ala—Ala—Pro—Glu—Val—Tyr—Ala—Phe—<br>CCG CGT GCT GCC CCG GAA GTC TAT GCG TTT |
| 449 | Ala—Thr—Pro—Glu—Trp—Pro—Gly—Ser—Arg—Asp—<br>GCG ACG CCG GAG TGG CCG GGG AGC CGG GAC |
| 459 | Lys—Arg—Thr—Leu—Ala—Cys—Leu—Ile—Gln—Asn—<br>AGG CGC ACC CTC GCC TGC CTG ATC CAG AAC |
| 469 | Phe—Met—Pro—Glu—Asp—Ile—Ser—Val—Gln—Trp—<br>TTC ATG CCT GAG GAC ATC TCG GTC CAG TGG |
| 479 | Leu—His—Asn—Glu—Val—Gln—Leu—Pro—Asp—Ala—<br>CTG CAC AAC GAG GTG CAG CTC CCC GAC GCC |
| 489 | Arg—His—Ser—Thr—Thr—Gln—Pro—Arg—Lys—Thr—<br>CGC CAC AGC ACG ACG CAG CCC CGC AAG ACC |
| 499 | Lys—Gln—Ser—Gly—Phe—Phe—Val—Phe—Ser—Arg—<br>AAG GCC TCC GGC TTC TTC GTC TTC AGC CGC |
| 509 | Leu—Gln—Val—Thr—Arg—Ala—Glu—Trp—Glu—Gln—<br>CTG GAG GTC ACC AGG GCC GAA TGG GAG CAG |
| 519 | Lys—Asp—Glu—Phe—Ile—Cys—Arg—Ala—Val—His—<br>AAA GAT GAG TTC ATC TGC CGT GCA GTG CAT |
| 529 | Glu—Ala—Ala—Ser—Pro—Ser—Gln—Thr—Val—Gln—<br>GAG GCA GCG AGC CCC TCA CAG ACC GTC CAG |
| 539 | Arg—Ala—Val—Ser—Val—Asn—Pro—Gly—Lys—[Stop]<br>CGA GCG GTG TCT GTA AAT CCC GGT AAA TGA |

The group X in Table V is a hydrogen atom or a chain initiating amino acid sequence, and, in the specific method of preparation which will be described below the group X is Met-Asp-Pro-Arg-, the corresponding nucleotide sequence being ATG GAT CCG CGC.

The invention further extends to polypeptide sequences of the types set out in Tables I and V above (as well as to those set out in Table I as modified by Table II, III or IV terminated at one or both of the N- and C-terminal ends by respective inert oligopeptide sequences initiating and/or terminating the chain.

Dimeric forms of the polypeptide competitors of the invention are of particular interest.

Also included within the scope of the invention are fragments of the polypeptides of the invention, including dimeric forms thereof, having competitive properties which are the same as or similar to those of the sequences defined above in Tables I and V or in Table I as modified by any one of Tables II to IV.

The invention also provides a host/vector system containing the nucleotide sequence which encodes the polypeptide of sequence 340 to 547.

The expression vector may conveniently be *Escherichia coli* N4830, and a culture of same harbouring a plasmid (designated as pE3–4) which encodes the peptide of sequence 34.0 to 547 has been deposited with the National Collection of Type Cultures in London on 18th November 1987 under the Accession Number NCTC 12162.

The invention also provides a method of preparing the polypeptide 340 to 547 comprising culturing the said host organism and isolating the peptide from the culture.

This invention also includes a pharmaceutical preparation in which the active principle is a polypeptide competitor for Immunoglobulin E low affinity receptor sites of the type defined above.

The preparation may also include a pharmaceutical carrier permitting administration of the polypeptide competitor in an appropriate manner, for example intranasally.

The polypeptide competitor of the invention may also be covalently linked to or associated with other therapeutic or diagnostic agents or other molecules with the effect that the polypeptide acts to target the therapeutic or diagnostic-agent to cells bearing IgE low affinity receptors.

The invention further contemplates use of the polypeptide competitors of the invention, their dimeric forms and biologically active fragments thereof in a binding assay and for inclusion in a diagnostic kit.

Thus, it has now been discovered that the polypeptide 340–547 of this invention has the ability to bind to the low affinity IgE receptors on cells. An advantage accruing from the invention is that the ability to distinguish between the high and low affinity binding sites of IgE enables separate administration of these effector molecules as may be medically indicated. IgE is associated with allergic reaction known as Type I immediate hypersensitivity and its value as an antagonist is discussed in our co-pending patent application identified above.

The reaction of IgE with mast cells not only leads to immediate hypersensitivity, but is directly responsible for setting up the conditions for delayed hypersensitivity, which is initiated by the release of chemical compounds from mast cells in the initial immune response. Delayed hypersensitivity involves an array of other cell types, such as platelets, macrophages and eosinophils, which are attracted to and cause an inflammatory response at the site of foreign body or initial tissue insult.

When these cells bind via the low affinity receptors to IgE and antigen, cytotoxic oxygen radicals are released which destroy cells in the local vicinity, including foreign cells if present. Thus, the polypeptide 340–547 may be considered for use as an antagonist of YgE to block or diminish the delayed hyper-sensitivity reaction associated with the natural IgE binding.

The invention will now be described by way of example. In the drawing.

Figure 1:
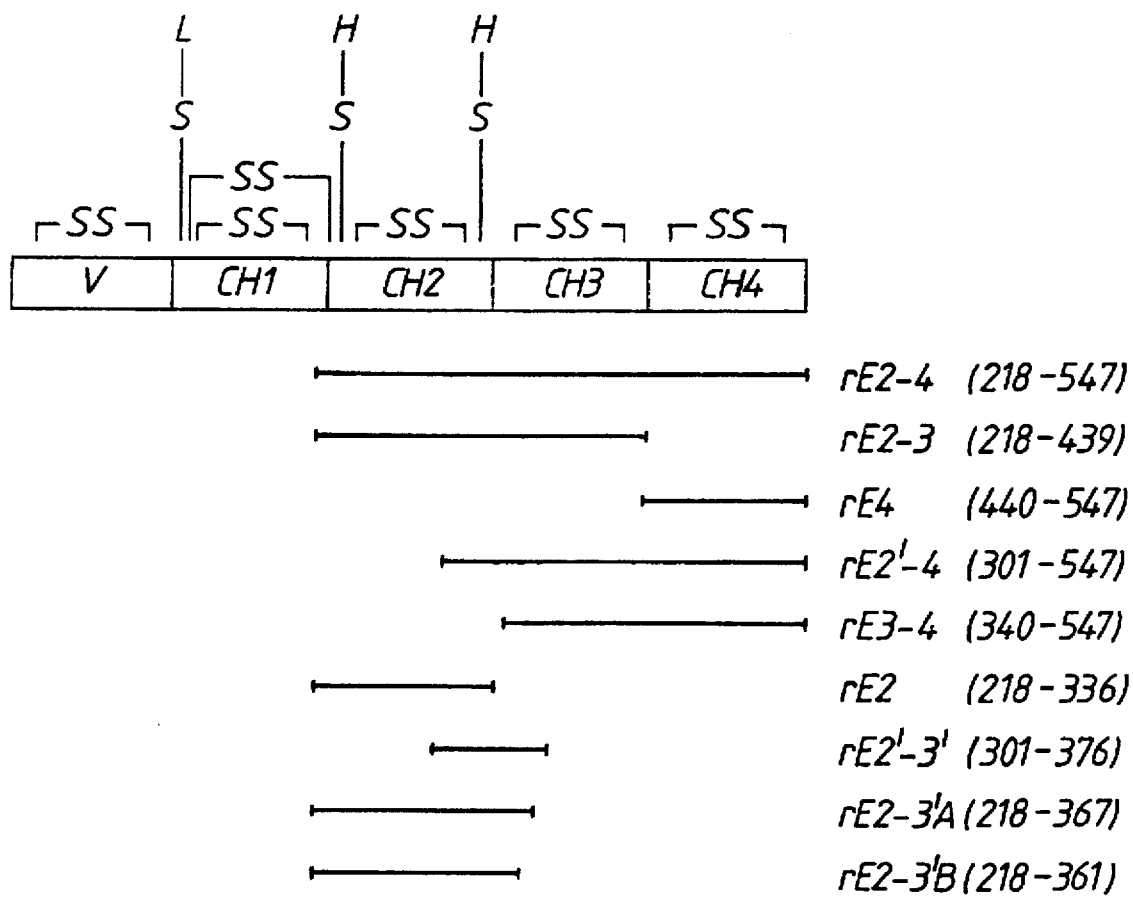
FIG. 1 shows the covalent structure of the human epsilon chain of IgE.

FIG. 1 shows the covalent structure of the human epsilon chain of IgE, indicating the positions of the intra-chain disulphide (S-S) bonds and inter-chain disulphide (S-S, S-L), and the boundaries of the five structural domains (VH, CH1–4), corresponding to exons in the genomic DNA, between the N-terminus (left) to the C-terminus (right). The recombinant peptides are described as follows: rE2–4 contains Asp 218-Lys 547 (Ce2–4 with seven amino acids from CH1); rE2–3 contains Asp218-Pro 439 (CH2 and CH3 with seven 440-Lys 547; rE2–4 contains Gln 301-Lys 547 (the C-terminal end of CH2 from the indicated position between the two cysteines that form the inter-chain disulphide bond, CH3 and CH4); rE3–4 contains Leu 340 Lys 547 (all but nine residues at the N-terminus of CH3 and CH4); rE2 contains Asp 218-Val 336 (CH2 with seven amino acids from CH1 and six from CH3); rE2'3' contains Gln 301 Arg 376 (the C-terminal part of CH2 and the N-terminal part of CH3 from the indicated positions between the cysteines that form intra-chain disulphide bonds in these domains).

Method

The genetic constructs used for expression in *E. coli* to yield the above peptides are described as follows: plasmids pE2–4 encoding rE2–4 and plasmid pE4 encoding E4 contain epsilon cDNA fragments bounded by Hind III sites and direct the synthesis of short N-terminal fusions containing the first seven amino acids of the Trp E sequence. The epsilon sequence in pE4 was inserted after addition of an 8-mer Hind III linker (New England Biolabs) to codon 439, the position of an FnuD II site. Plasmid pE2 is a derivative of pE2–4 modified by a 12-mer Nhe I linker (New England Biolabs), which provides translation stop signals. This linker was ligated only to codon 337 in the epsilon sequence after cleavage of the cloned cDNA by Hae II and removal of the 3' overhang with T4 polymerase. Plasmid pE2–3 comprises an epsilon cDNA fragment subcloned into ptac-85 and directs the expression of a non-fusion polypeptide. A translation termination signal (P.L. Biochemicals) was placed immediately downstream of the CH3 sequence by ligating a synthetic oligonucleotide to codon 439, after cleavage of the epsilon sequence at that position with FnuD II. Plasmid pE2'-4 encoding rE2'-4' contains an epsilon gene fragment, which, after cleavage with Sac I (cutting at codon 297) and mild exonuclease treatment with Bal 31, was inserted into the expression vector pASl. The plasmid pE2'-3' encoding rE2'-3' was made by insertion of a translation terminator into pE2'-4 at the Sma I restriction site located at codon 376.

The rE3–4 sequence was synthesised in *E. coli* under control of the lambda PL promoter in pE3–4, a recombinant derivative of pASI (Rosenberg et.al., 1983, Meths. Enzymol. 101, 123–138). The gene fragment in pE3–4 was tailored for insertion into the BamgI site of pASI after cleavage of the epsilon DNA with HaeII, mild exonuclease treatment and addition of a 12-mer BamHI linker. The DNA sequence around the BamHI site was determined; from this the deduced amino acid sequence showed that the expressed epsilon sequence started at codon 340. Additional residues introduced in the manipulation are:

| ATGGATCCGCGC... CTA |
|---|
| Met-Asp-Pro-Arg ... Leu— |

(residue 340 of epsilon sequence)

In *E. coli* N4830 the epsilon gene fragment in pE3–4 can be expressed by heat induction. To achieve this, growth of the strain to A600=0.8 at 30° C. (non-inducing) is followed by incubation at 42° C. (inducing).

The site on human IgE involved in the binding to the low affinity ($FcER_2$) sites on the $FcER_2$- positive human B cell line RPMI 8866 was probed using cloned fragments of human IgE generated in *E. coli* from the deletion mutants of the gene encoding the CH2, CH3 and CH4 domains of the epsilon (ND) heavy chain. Preliminary indirect and direct immunofluorescence binding assays were carried out on the various fragments and the results are given in Table VI below which is an indication of the ability of each peptide to bind to the high affinity receptor.

TABLE VI

Summary of binding of recombinant IgE peptides to human high-affinity ($FcR_1$) and low-affinity ($FcR_2$) receptors.

| Peptide | Amino Acids | Heavy Chain Domains | | | | | Binding | |
|---|---|---|---|---|---|---|---|---|
| | | VH1 | CH1 | CH2 | CH3 | CH4 | FcER1 | FcER2 |
| IgE | 1—547 | + | + | + | + | + | + | + |
| rE2-4 | 218—547 | – | – | + | + | + | + | + |
| rE2'-4 | 301—547 | – | – | part | + | + | + | + |
| rE2-3 | 218—439 | – | – | + | + | – | + | – |
| rE2'-3' | 301—376 | – | – | part | part | – | + | – |
| rE4 | 440—547 | – | – | – | – | + | – | – |
| rE2 | 218—336 | – | – | + | – | – | – | – |
| rE3-4 | 340—547 | – | – | – | + | + | – | + |

These results indicate that the binding of human IgE to $FcER_2$ requires the presence of the third and fourth domains of the heavy chain, as given by the polypeptide of the present invention and that, of our peptides tested, only the peptide rE3–4 binds to the low affinity receptors to the exclusion of high affinity binding.

Further indirect immunofluorescence studies confirmed that the myeloma protein IgE (PS), rE2–4, rE2'–4 and rE3–4 bound to ≧90% of $FcER_2$ positive RPMI 8866 B cells. However, this further work showed that, by contrast, there was no detectable binding of rE2-3, rE2'-3', rE4 and rE2. The binding of the rE peptides was specific, since it could be inhibited by preincubation of the cells with two anti-$FcER_2$ monoclonal antibodies (mAb 135 and anti-BLAST-2), but not by control IgG1 of unrelated specificity. Moreover, it was found that there was no binding to the $FcER_2$ negative cell lines Jurkat and Raji.

Binding ability of rE peptides

RPMI 8866 cells were incubated with different concentrations of rE peptides and indirect immuno-fluorescence was performed.

For indirect immunofluorescence the results of which are summarised in Table VII, 0.5×10⁶ RPMI 8866 cells (>99% $FcER_2$ positive) in staining buffer (RPMI 1640 - 2.5% fetal bovine serum, containing 0.01% azide) were incubated with various concentrations (0.1–200 µg/ml) of purified rE fragments or native IgE(PS) for 40 minutes at 4° C. After washing, the cells were incubated for 30 minutes at 4° C. with the appropriate fluorescein isothiocyanate (FITC)-conjugated anti-Fc mAB or with an affinity-purified goat anti-human IgE antibody (10 µg/ml). After extensive washing, the percentage of cells binding IgE or the rE fragments was evaluated by a FACScan (Becton Dickinson, Mountain View, Calif.). Table VII shows the absolute percentage of positive cells (mean ±S.D. of results obtained in 9 experiments).

TABLE VII

Binding of recombinant IgE peptides to RPMI 8866 B cells by indirect immunofluorescence

| Ligand | Amino acid sequence | % positive cells |
|---|---|---|
| IgE (PS) | Glp 1—Lys 547 | 91 ± 2% |
| rE2-4 | Asp 207—Lys 547 | 92 ± 2% |
| rE2'-4 | Gln 299—Lys 547 | 91 ± 2% |
| rE3-4 | Leu 330—Lys 547 | 90 ± 3% |
| rE2-3 | Asp 207—Pro 439 | 3 ± 1% |
| rE2'-3' | Gln 291—Arg 376 | 2 ± 1% |
| rE2 | Asp 207—Val 336 | 2 ± 1% |
| rE4 | Arg 430—Lys 547 | 3 ± 2% |

The data of Table VII indicate that the $FcER_2$ binding site is contained in the rE3–4 peptide (Leu 340-Lys 547), and does not require the CH2 domain.

For the tests using anti-$FcER_2$ monoclonal antibodies, 0.5×10⁶ RPMI 8866 cells in staining buffer were preincubated with medium, anti-$FcER_2$ mAbs (mAb 135 or anti-BLAST-2 mAb), 1 µg/ml, or a control IgG1 murine mAb (anti-HLA-DP, 2.5 µg/ml) for 60 minutes at 4° C. After washing, the cells were incubated for 40 minutes at 4° C. with IgE(PS) (1 µg/ml) or rE3–4 (200 µg/ml), followed by mAb RPI-FITC. Table VIII shows the absolute percentage of positive cells (mean±S.D. of results obtained in 3 experiments).

TABLE VIII

Anti-FcER₂/CD23 mAbs inhibit the binding of rE3-4 to RPMI 8866 cells

| Inhibitor | Ligand | |
|---|---|---|
| | IgE | rE3-4 |
| Nil | 88 ± 2 | 89 ± 3 |
| mAb 135 | 2 ± 1 | 5 ± 2 |
| anti-BLAST-2 | 3 ± 1 | 4 ± 2 |
| control mouse IgG1 | 74 ± 2 | 76 ± 5 |

In these experiments the mAb 135 used was as described by E. Rector et al., Immunology, 55, 481–487 (1985), while the anti-BLAST-2 mAb was as described by C. Kintner et al, Nature, 294,458–460 (1981).

Figure 2:
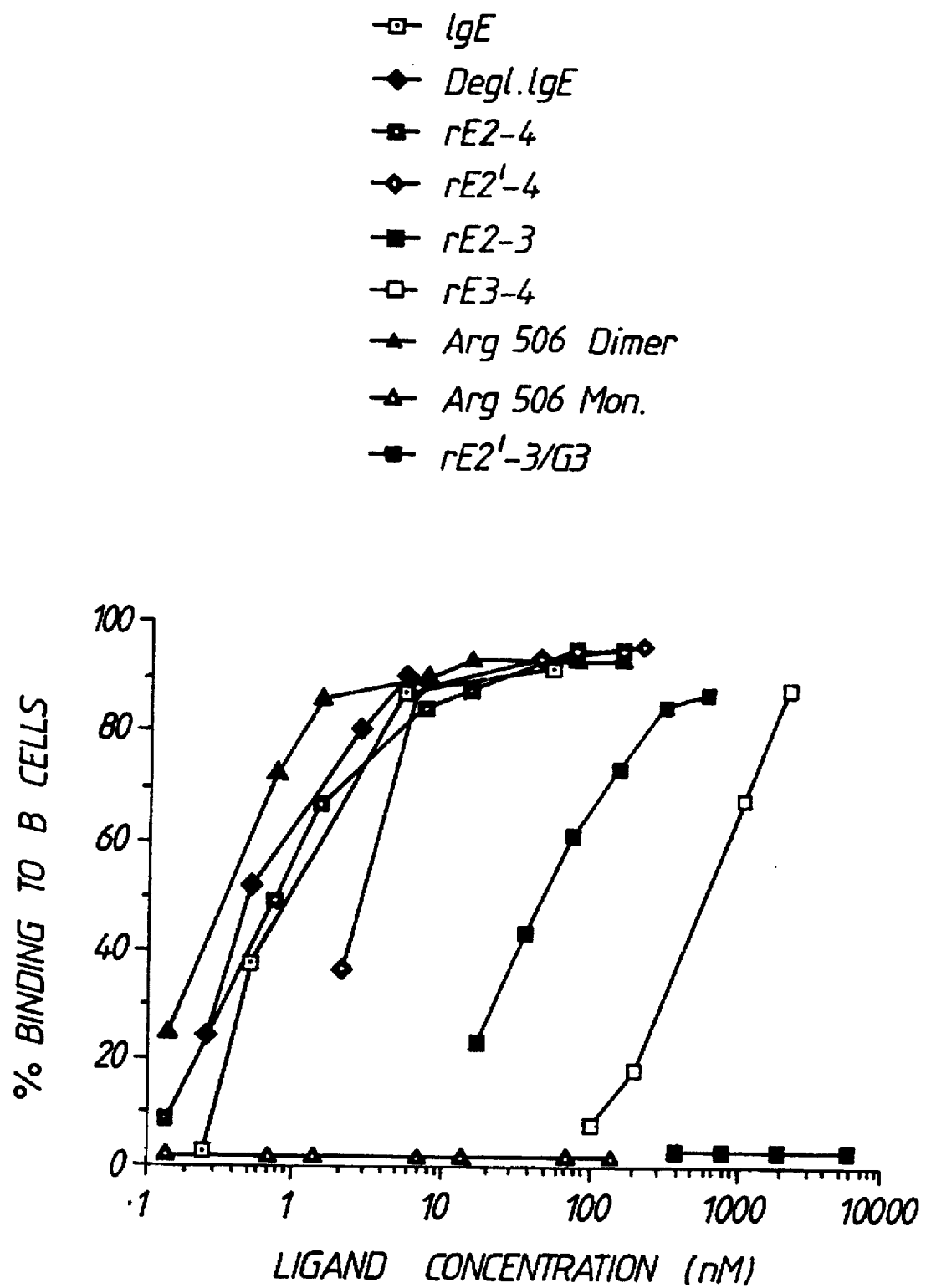
FIG. 2 illustrates the results obtained upon polyacrylamide gel electrophoresis of affinity-purified rE peptides.

To compare the relative activities of different epsilon-chain fragments and mutant sequences, binding has been measured as a function of peptide concentration. Binding profiles are shown in FIG. 2 and the results are summarised in Table IX. rE2'-3/G3 is a chimaeric recombinant which was constructed using mouse gamma-2b cDNA from pHG201, described by S. Roberts et al, Protein Engineering, 1, 59–65 (1986). The mouse CH3 sequence was derived by partial SacI digestion of pHG201 to yield a DNA fragment encoding amino acids 346–447 (EU index). This fragment was inserted downstream of codon 439 in pE2'14 4 replacing the C epsilon-4 sequence with the Cgamma-2b CH3 domain. The recombinant peptide reacted with both epsilon and gamma-2b antisera.

TABLE IX

Binding ability of rE peptides

| Ligand | Molarity required for 50% binding to B cells |
|---|---|
| IgE | 9.0 ± 10⁻¹⁰ |
| Deglycosylated IgE | 4.8 ± 10⁻¹⁰ |
| rE2-4 | 7.2 ± 10⁻¹⁰ |
| rE2'-4 | 2.6 ± 10⁻⁹ |
| rE3-4 | 5.8 ± 10⁻⁷ |
| rE2-4 Arg 506 (dimer) | 1.6 ± 10⁻¹⁰ |
| rE2'-3/G3 | 4.7 ± 10⁻⁸ |

For deglycosylation, IgE (PS) (200 µg/ml) in 0.55 M sodium phosphate, pH 8.6, was incubated with N-glycosydase F (N-Glycanase, Genzyme Corporation, Boston, Mass.), 15 U/ml, at 37° C. overnight, and subsequently absorbed with an excess of Lentil Lectin Sepharose 4 B (Sigma Chemical Company, St. Louis, MO) at 4° C. on rotation. Analysis of the preparation by SDS-PAGE and periodic acid-Schiff (PAS) staining of the gel showed that complete deglycosylation of IgE had occurred. IgE concentration in the deglycosylated sample was assessed by radio-immunoassay.

The point substitutions in rE2-4 were carried out by oligonucleotide-directed site specific mutagenesis using double-stranded plasmid DNA in accordance with the procedures described by Y. Morinaga et al, Biotechnology, July, 636–639 (1984).

The recombinant Fc(rE2–4) is highly active, indeed perceptibly more so than myeloma IgE (PS). The elevated affinity is presumably due to the absence of carbohydrate, since our results showed that enzymatic deglycosylation of IgE (PS) increased its activity. rE3–4, which lacks CH2 and nine amino acids from CH3, displayed a much lower activity than rE2-4. A truncated peptide, rE2'-4, retaining the C-terminal thirty amino acids of CH2, by contrast, was almost as active as the full Fc sequence. For physiological binding affinity, therefore, all three Fc domains appear to be necessary.

The structural elements of Fc necessary for binding were defined. The Fc regions of all classes of antibodies are thought to have a number of common features. In particular, they contain two heavy chains, non-covalently linked in their C-terminal domains (e.g. CH4 or C-gamma 3), separated by carbohydrate in the middle domain (CH3 or C-gamma 2), and covalently linked by one or more disulphide bonds in the N-terminal domain (CH2 in IgE, corresponding to the hinge region of IgG). The inter-chain linkages in CH2 and CH4 thus generate a tertiary structure, which may be required for receptor recognition. To determine whether this defines the active state, the activity of monomeric chains has been examined.

All rE chain fragments that contain the CH4 domain can form dimers in solution. All three Fc domains are found to be necessary, however, for the formation of disulphide-linked dimers, suggesting that the non-covalent association in CH4 is required to place the thiols in register in CH2, so that disulphide bond formation can occur. If the association of two CH4 domains nucleates dimer formation, it is conjectured that the formation of dimers could be inhibited by preventing this association. The IgE model suggests that the two Phe 506 residues in CH4 are in van der Waals contact. Thus the replacement of Phe 506 by a charged residue should oppose the formation of dimers. It has been found that the mutant gene expression product, rE2–4 (Arg 506), remains monomeric, as judged by gel electrophoresis. After elimination of a trace of dimer (<1%) by HPLC, we found the product to be completely inactive in binding to B cells. Strikingly, the dimer, recovered in a separate fraction, was more active than the unmutated Fc. Phe 506 is unlikely to form part of the recognition sequence, since it is buried in the CH4 domain. It is concluded that the dimerisation of chains is essential for FcER₂ binding.

Figure 3A:
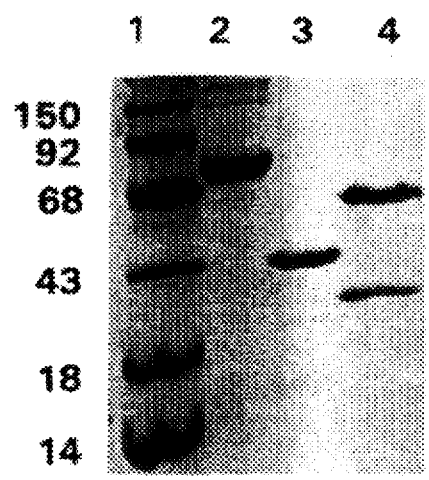
FIG. 3 shows results obtained with affinity purified rE peptides analysed in SDS-urea gel.
Figure 3B:
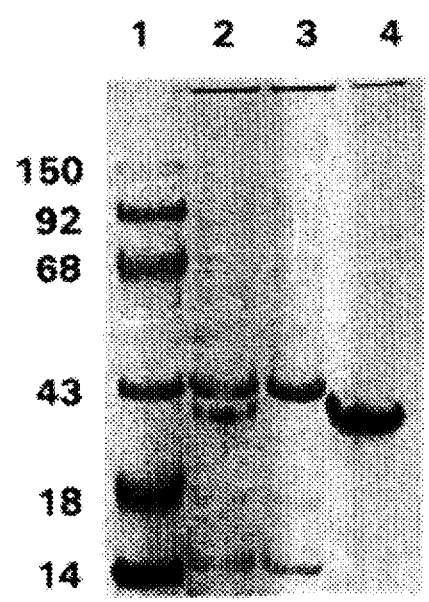

FIG. 2 illustrates the results obtained upon polyacrylamide gel electrophoresis of affinity-purified rE peptides. In FIG. 3 A designates the results obtained with peptides analysed in a 20% SDS-urea gel under non-reducing conditions, while B shows the results obtained with peptides analysed in a 15% SDS-urea gel under reducing conditions. The order of sample application was: lane (1) standard proteins, lane (2) rE2–4, lane (3) rE2–4 (Arg 506), land (4) rE2'–3/G3. The peptides were isolated from E coli and affinity-purified.

Since CH4 is required for dimerisation and dimerisation for activity, the possibility that part of the binding site lies in CH4 could not be excluded by simply deleting this domain. The monomeric state of rE2–3, for example, is sufficient to account for its inactivity in the binding assay summarised in Table VII above. To define the role of CH4 sequences in FcER₂ binding, an investigation was made of the behaviour of the chimaeric immunoglobulin fragment, rE2'–3/G3, in which the C-terminal domain of rE2'–4 is replaced by that of a mouse gamma-2b chain. As expected from the homology between IgE and IgG, the chimaeric chains form disulphide-linked dimers in high yield, as can be seen from FIG. 3 which shows the results obtained with rE peptides analysed in a 20% SDS-urea gel under non-reducing and reducing conditions. The dimers displayed a level of activity within an order of magnitude of that of their non-chimaeric counterpart as can be appreciated by inspection of FIG. 2 which illustrates the results obtained upon polyacrylamide gel electrophoresis of affinity purified rE peptides. Since it was found also that mouse IgG2b did not bind to the B cells, it is concluded that the FcER2-specific binding site is located in CH3.

To map the FcER$_2$ binding site on the CH3 domain more precisely, there were used monoclonal antibodies (mAbs) against epitopes in the Fc region and their efficiency in inhibiting the binding of $^{125}$I-labelled IgE to B cells was measured. The various epitopes recognised by the antibodies were mapped to the rE peptides by Western blotting, and the locations of peptides in the sequence were related to their positions in the model. The results are summarised in Table X.

TABLE X

Anti-human Fc mAbs: specificity and inhibition of $^{125}$I-IgE binding to FcER$_2$

| mAb | epitope location (amino acids) | % inhibition of $^{125}$I-IgE binding |
|---|---|---|
| DC | CH2 (Asn 218—Gln 301) | none |
| AS 7.12 | CH2 (Asn 218—Gln 301) | none |
| BS 17 | CH2 (Gln 301—Thr 315) | 78 |
| RP 3 | CH2 (Asp 307—Thr 315) | 77 |
| IC 272 | CH2 (Thr 315—Val 336) | 22 |
| Le 27 | CH3 (Leu 340—Val 361) | none |
| RP 1 | CH3 (Leu 340—Val 361) | none |
| IC 27 | CH3 (Lys 367—Val 370) | 88 |
| IC 173 | CH4 (Arg 440—Lys 547) | none |

The specificity of the anti-Fc mAbs was deduced by their pattern of reactivity with the rE fragments, rE fragments containing amino acid residues Asp 218-Thr 315 and a synthetic peptide comprising amino acid residues Asp 307-Val 370 in enzyme-linked immunosorbent assay, Western blot and dot immunoassay. Purified human myeloma IgE (PS) was iodinated by the chloramine-T method (specific activity: 8000 cpm/ng). To test the ability of the anti-Fc mAbs to inhibit the binding of IgE to FcER$_2$, $^{125}$I-IgE (15 ng in 50 µl) in PBS-0.5% BSA was mixed with a 10,100, 1000 M excess of anti-Fc mAbs for 1 hour at 37° C., and then added to 1×10$^6$ RPMI 8866 cells in 0.1 ml. After incubation for 2 hours at 4° C., the cells were spun through serum and the cell-bound radioactivity was counted. Maximal binding was determined by incubating the cells with $^{125}$I-IgE in the presence of medium alone. Table X shows the inhibition obtained with a 10 M excess of mAb.

Three of the nine monoclonal antibodies strongly inhibited the IgE-receptor interaction. The epitopes for mAb BS 17 and RP 3-lie in the C-terminal region of CH2 (between Gln 301 and Thr 315) and that for the third, IC 27, is at the N-terminal end of CH3 (comprising Lys 357-Val 370). The three sites are located within or near to the cleft between the CH2 and CH3 domains in the model of Fc. A fourth mAb, IC 272, which binds in an intervening sequence (Thr 315-Val 336) was only weakly inhibitory. It is envisaged that this mAb binds to the loop separating the two beta-strands that line the cleft between the CH2 and CH3 domains on the CH2 side. This would afford an explanation for its rather weak inhibitory effect. Two other mAbs, RP 1 and Le 27, which bind within a second intervening sequence (Leu 340-Val 361), had no inhibitory effect. The whole of this peptide segment points away from the cleft. Three other mAbs, DC, AS 7.12 and IC 173, which bind to epitopes outside the CH2–CH3 junction region, in CH2 and CH4, did not inhibit receptor binding. Taken together with the results of the fragment binding assay, these data suggest that FcER$_2$ binds in the vicinity of Asp 362 -Val 370. Since CH2 does not contribute sequences to the binding site, inhibition by anti-CH2 mAbs can result only from steric hindrance.

The results discussed above show that the FcER$_2$ binding site on human IgE lies in the N-terminal region of CH3, close to CH2 in the 3D structure of Fc. However, the CH4 and CH2 domains determine the level of activity through their effects on the structure of CH3. In particular, it is found that both CH3 domains are required for activity; CH2 and CH4 serve only to generate a dimer. The native structure in CH2 does not appear to be important per se, since the truncated CH2 domain in rE2'–4 suffices for nearly full activity, and rE3–4 is also active. That in CH4 may also be dispensed with, once covalent bonds are formed, since the substitution of Phe 506 by arginine did not impair activity in the dimer.

The observation that the chimaeric peptide, rE2'-3/G3, displayed significantly less than full activity in binding to the B cell FcER$_2$ requires comment. It is suggested that the C-terminal domain in native IgE may interfere with the binding of IgE to FcER$_2$, and that CH4 constitutes a smaller obstacle to binding than C-gamma-3. It was found that rE2–4 (Arg 506) is more active as a dimer than rE2–4; this might be due to the presence of unpaired CH4 domains, which, owing to their segmental flexibility and rotational freedom, might interfere to a lesser extent than the paired domain. rE4, which appears to have a native structure by the criterion of dimerisation, failed to bind to the FcER$_2$ on the B cell. It is therefore unlikely that the CH4 domain makes a positive contribution to the interaction of IgE with FcER$_2$.

The data do not reveal whether both C-epsilon domains bind to a single receptor or whether one, or possibly two, FcER$_2$ molecules bind to the separate CH3 domains in a dimer. The first (2:1) model of binding seems unlikely, since the two CH3 domains are far apart, being separated by protein and carbohydrate. Existing evidence is inconclusive. It has been shown that mAb IC 27 can bind to an IgE, immobilised on its receptor on a B cell. This could imply that the FcER$_2$ molecule binds to only one of the CH3 domains of IgE, leaving the second free to interact with the mAb (if it is assumed that the mAb and the receptor compete for the same site). Other data, however, suggest that two receptors may bind to the CH3 domains on a single IgE molecule, for a bivalent monoclonal antibody against murine FcER$_2$ binds to the same number of sites as does IgE, while its Fab' fragment binds to twice this number. In theory, "monogamous bivalency", as the 2:2 binding mode has been termed, may offer a large gain in affinity, via. $K_a$ dimer $\geq (K_a$ monomer)$^2$. If the observed $K_a$ of $10^7$ M$^{-1}$ arises from comparable contributions at both sites, then the binding free energy developed by a single-site interaction may be below the threshold of detection used in the assay described herein. There is still uncertainty about the stoichiometry of the interaction which translates into a question of specificity, namely whether or not the receptor recognises a single CH3 domain in a conformation induced by dimerisation, or whether or not the dimer serves only to generate higher affinity through interaction at two sites.

The FcER$_2$ binding site is distinct from the FcER$_1$ binding site in human IgE: FcER$_1$, but not FcER$_2$, binds to rE2–3 and rE2'-3', whereas FcER$_2$, but not FcER$_1$, binds to rE3–4. This indicates that some part of the sequence between Gln 301 and Leu 340 is required for FcER$_1$, but not for FcER$_2$ binding. The sites may overlap in CH3, in the region between Val 362 and Lys 367, which forms the C-terminal boundary of the FcER$_1$ site, but the FcER$_2$ site may extend further towards the C-terminal side, or indeed the sites may be totally separate. Higher-resolution mapping is required to establish the N-terminal boundary of the FcER$_2$ binding site and thus determine the extent, if any, of common sequence.

The two receptors also exhibit a different mode of binding, since $FcER_1$ binds to monomeric and dimeric chains, wherein $FcER_2$ fails to bind to monomers. The monocyte receptor binding site on IgG1 and the T and B cell receptor binding site on IgM have been mapped, respectively, to the C-gamma-2 and C-mu-3 domains, homologous to CH3. It is of interest that Fc-mu-R, like $FcER_2$, fails to bind to monomeric chains.

$FcER_1$ and $FcER_2$ are unrelated proteins; $FcER_1$ belongs to the immunoglobulin superfamily, in common with all other immunoglobulin receptors so far described. $FcER_2$ is unique, in that it is homologous to the asialoglycoprotein receptor. It is therefore surprising that $FcER_2$ binds to rE2-4, and to enzymatically deglycosylated IgE, even more strongly than to native IgE. High affinity binding of IgG to Fc-gamma-R1, on the contrary, is reported to be dependent on the presence of carbohydrate. It is noted that there is a glycosylation site at Asn 371 in the epsilon chain near the putative region of the $FcER_2$ binding site. This carbohydrate substituent is clearly not a part of the binding site, but it is found only in epsilon-heavy chains and might be well placed to modulate $FcER_2$ binding activity.

We claim:

1. A polypeptide competitor which is specific for Immunoglobulin E low affinity receptor sites and which is a dimer of a polypeptide having the sequence of amino acid residues, numbered 340 to 547, according to the Bennich enumeration, of the formula:

| | |
|---|---|
| 340 | X—Leu—Ser—Arg—Pro—Ser—Pro—Phe—Asp—Leu— |
| 349 | Phe—Ile—Arg—Lys—Ser—Pro—Thr—Ile—Thr—Cys— |
| 359 | Leu—Val—Val—Asp—Leu—Ala—Pro—Ser—Lys—Gly— |
| 369 | Thr—Val—Asn—Leu—Thr—Trp—Ser—Arg—Ala—Ser— |
| 379 | Gly—Lys—Pro—Val—Asn—His—Ser—Thr—Arg—Lys— |
| 389 | Glu—Glu—Lys—Gln—Arg—Asn—Gly—Thr—Leu—Thr— |
| 399 | Val—Thr—Ser—Thr—Leu—Pro—Val—Gly—Thr—Arg— |
| 409 | Asp—Trp—Ile—Glu—Gly—Glu—Thr—Tyr—Gln—Cys— |
| 419 | Arg—Val—Thr—His—Pro—His—Leu—Pro—Arg—Ala— |
| 429 | Leu—Met—Arg—Ser—Thr—Thr—Lys—Thr—Ser—Gly— |
| 439 | Pro—Arg—Ala—Ala—Pro—Glu—Val—Tyr—Ala—Phe— |
| 449 | Ala—Thr—Pro—Glu—Trp—Pro—Gly—Ser—Arg—Asp— |
| 459 | Lys—Arg—Thr—Leu—Ala—Cys—Leu—Ile—Gln—Asn— |
| 469 | Phe—Met—Pro—Glu—Asp—Ile—Ser—Val—Gln—Trp— |
| 479 | Leu—His—Asn—Glu—Val—Gln—Leu—Pro—Asp—Ala— |
| 489 | Arg—His—Ser—Thr—Thr—Gln—Pro—Arg—Lys—Thr— |
| 499 | Lys—Gln—Ser—Gly—Phe—Phe—Val—Phe—Ser—Arg— |
| 509 | Leu—Gln—Val—Thr—Arg—Ala—Glu—Trp—Glu—Gln— |
| 519 | Lys—Asp—Glu—Phe—Ile—Cys—Arg—Ala—Val—His— |
| 529 | Glu—Ala—Ala—Ser—Pro—Ser—Gln—Thr—Val—Gln— |
| 539 | Arg—Ala—Val—Ser—Val—Asn—Pro—Gly—Lys—[Stop] | wherein X is a hydrogen atom or a chain initiating amino acid sequence.

2. A polypeptide competitor according to claim 1 in which X represents a hydrogen atom.

3. A polypeptide competitor according to claim 2, in which X represents Met-Asp-Pro-Arg-.

* * * * *